Figure 3:
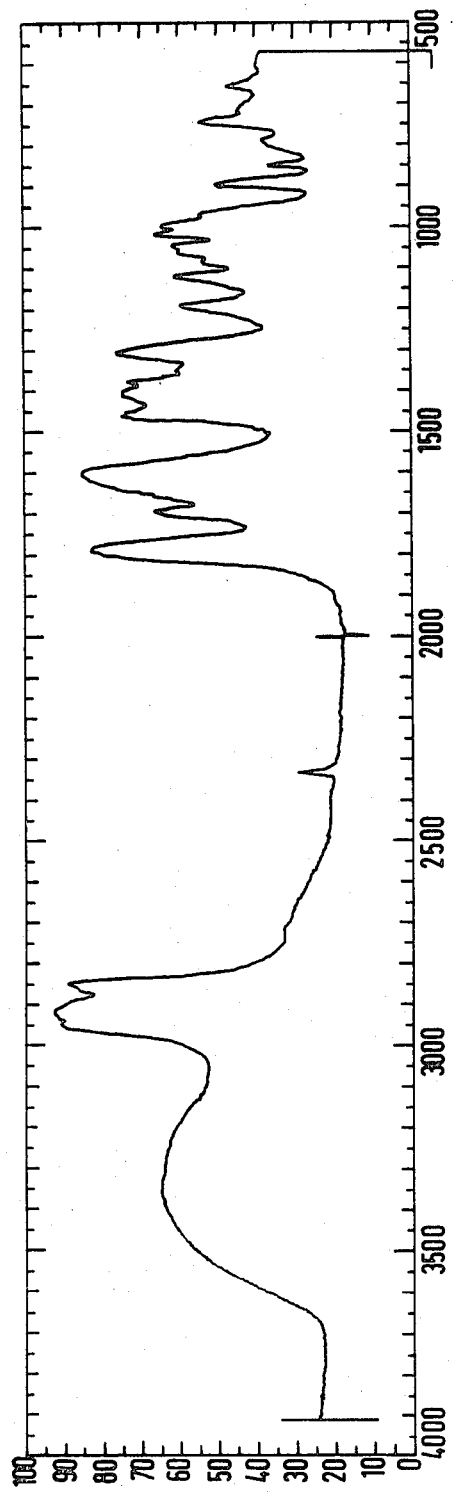

United States Patent [19]

Fleming et al.

[11] 4,367,175

[45] Jan. 4, 1983

[54] PURE POTASSIUM SALT OF CLAVULANIC ACID

[75] Inventors: Ian D. Fleming, Chalfont St. Peter; David Noble; Hazel M. Noble formerly Gillett, both of Marlow; Wilfred F. Wall, High Wycombe, all of England

[73] Assignee: Glaxo Laboratories Limited, Middlesex, England

[21] Appl. No.: 147,614

[22] Filed: May 7, 1980

Related U.S. Application Data

[60] Division of Ser. No. 888,496, Mar. 20, 1978, Continuation of Ser. No. 654,638, Feb. 2, 1976, abandoned.

[30] Foreign Application Priority Data

Feb. 7, 1975 [GB] United Kingdom ................. 5409/75
Mar. 17, 1975 [GB] United Kingdom ............... 11076/75

[51] Int. Cl.³ .................... C07D 498/04; A61K 31/42
[52] U.S. Cl. .................................. 260/245.3; 424/272
[58] Field of Search ..................................... 260/245.3

[56] References Cited

U.S. PATENT DOCUMENTS 4,301,149  11/1981  Crowley .............................. 424/114

FOREIGN PATENT DOCUMENTS 1315177  4/1973  United Kingdom .

OTHER PUBLICATIONS

Anon, *Scrip* #430, 10-17-79.
Beecham Data Sheet, "Augmentin-A Major Breakthru in Antibiotic Therapy", Sep. 1981.
Veitch, The Guardian of 9-12-81, "Resistant Bacteria Fall to New Drug".

*Primary Examiner*—Mark L. Berch
*Attorney, Agent, or Firm*—Bacon & Thomas

[57] ABSTRACT

The invention provides the compound (2R,5R,Z)-3-(2-hydroxyethylidene)-7-oxo-4-oxa-1-azabicyclo-[3,2,0]-heptane-2-carboxylic acid and its salts in purified form and pharmaceutical compositions containing them and a process for the purification of such compounds by conversion in aqueous media to the lithium salt of the above acid and precipitation thereof.

1 Claim, 3 Drawing Figures

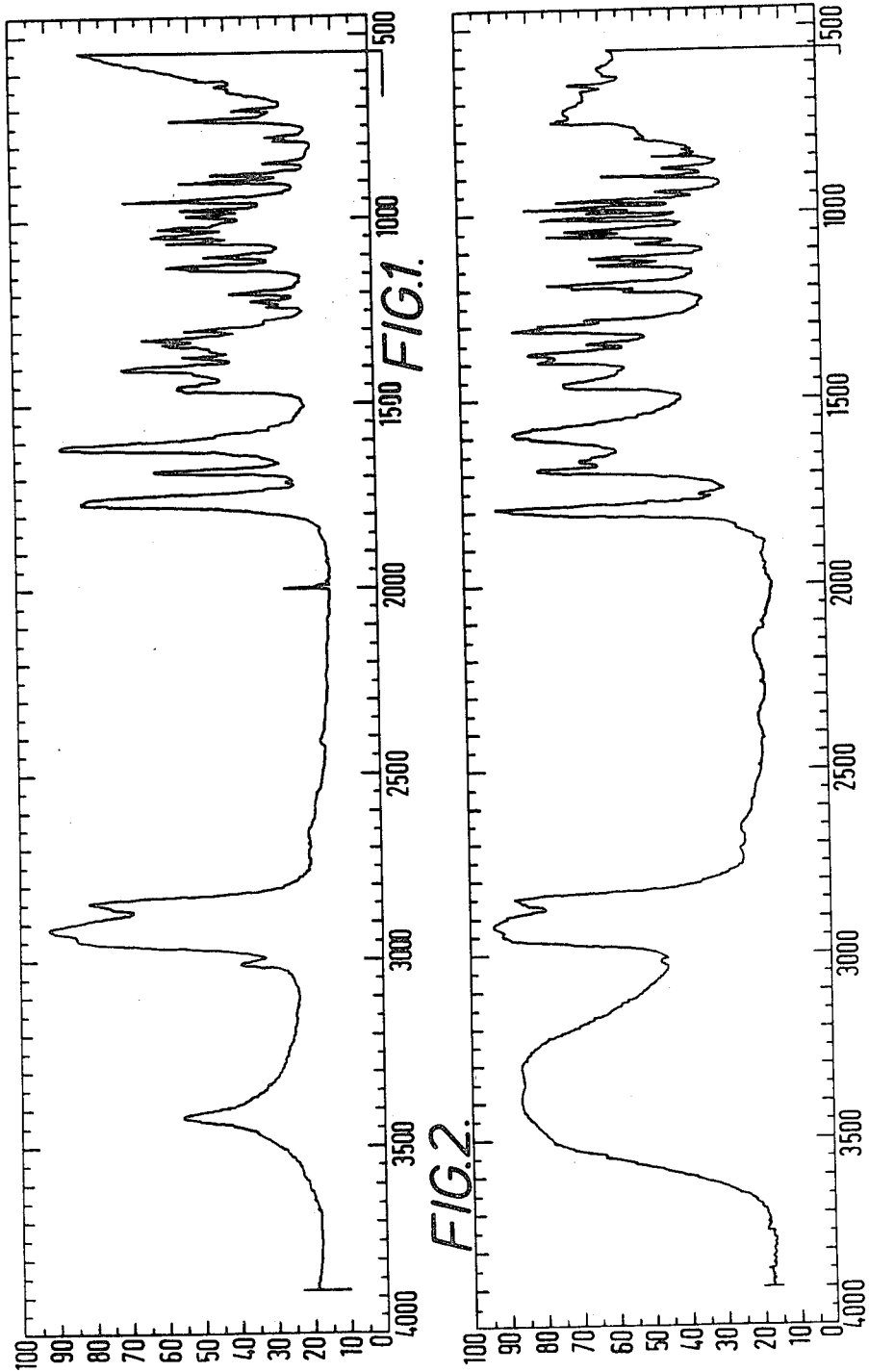

PURE POTASSIUM SALT OF CLAVULANIC ACID

This is a division, of pending application Ser. No. 888,496 filed Mar. 20, 1978 as a continuation of application Ser. No. 654,638, filed Feb. 2, 1976, now abandoned.

This invention relates to a novel antibiotic and its salts and to a process for their production in pure form.

Fermentation of *Streptomyces clavuligerus*, and in particular strain NRRL 3585, is known to produce a number of antibiotic substances and thus British Patent Specification No. 1,315,177 describes and claims the cultivation of *Streptomyces clavuligerus* strain NRRL 3585 until a substantial amount of two antibiotics, referred to as Antibiotics A 16886 I and A 16886 II, is produced.

We have now found that a further antibiotic may be obtained from this organism, namely (2R, 5R, Z)-3-(2-hydroxyethylidene)-7-oxo-4-oxa-1-azabicyclo[3,2,0-]heptane-2-carboxylic acid having the formula I

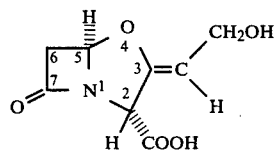

hereinafter termed for convenience 'clavulanic acid'. The present invention includes this compound and also its salts.

Salts according to the invention include the alkali metal salts, e.g. the sodium, potassium and lithium salts; alkaline earth metal salts, e.g. calcium, magnesium and barium salts; the ammonium salt; and organic base salts for example salts derived from primary, secondary, tertiary or N-quaternary amines, e.g. mono, di- or trialkylammonium salts such as methylammonium and triethylammonium salts and heterocyclic base salts such as piperidinium salts.

The inorganic base salts and most of the organic base salts are, in general, more stable in aqueous solution than free clavulanic acid. The salts may exist in the form of solvates, i.e. having water and/or other solvent of crystallisation.

We have obtained clavulanic acid and its salts at a purity of at least 75% and in general at least 85% i.e. having not more than 25%, and generally not more than 15%, by weight of impurities and isomers arising from production.

Furthermore, using the technique described hereinafter, clavulanic acid salts have been obtained in an even higher degree of purity, being substantially free from impurities and isomers arising from production for example having purities of 98% or greater, i.e. containing less than 2% by weight of impurities or isomers arising from production. We have thus prepared lithium clavulanate and several other clavulanate salts in crystalline form. These salts were substantially pure as shown by molar extinction coefficients, determined at 259±1 nm in 0.1 M aqueous sodium hydroxide, of at least 16,200. The molar rotations $[M]_D^{24}$ values in aqueous solution, were +137°±5°. The free acid, as prepared from its salts, has shown an extinction coefficient, $E_{1\,cm}^{1\%}$ in 0.1 M aqueous sodium hydroxide at 259 nm of 590 or greater and a specific optical rotation $[\alpha]_D^{24}$ in dimethyl sulphoxide, of about +54°. It will be appreciated that production of material of this level of purity enables the products to be used in pharmaceutical and veterinary compositions and is highly desirable for use of materials as intermediates.

The term 'purity' as used herein refers to the percentage of clavulanic acid and/or salt thereof expressed in terms of the total solids present on a weight basis but excluding associated water or other solvents.

Clavulanic acid and its salts have antibacterial activity against a range of gram-negative and gram-positive microorganisms, for example against strains of *Staphylococcus aureus, Escherichia coli, Salmonella typhimurium, Shigella sonnei, Enterobacter cloacae, Klebsiella aerogenes, Proteus mirabilis, Proteus morganii, Serratia marcescens,* Providencia species, *Citrobacter koseri, Haemophilus influenzae* and Bacteroides species.

Clavulanic acid and its salts are stable to the action of β-lactamases produced by gram-positive organisms, for example those produced by *Staphylococcus aureus* and *Bacillus cereus,* and to the β-lactamases produced by gram-negative organisms in classes I–V described by Richmond, M. H. and Sykes R. B. (1973). ("The β-lactamases of gram-negative bacteria and their possible physiological role." Advances in Microbial Physiology, 9, 31–88).

Clavulanic acid and its salts also possess the ability to inhibit β-lactamase enzymes produced by gram-positive organisms, for example those produced by strains of *Staphylococcus aureus* and *Bacillus cereus* and also the enzymes classified in classes II–V from gram-negative bacteria produced by organisms such as strains of *Proteus mirabilis, Escherichia coli, Proteus morganii, Klebsiella aerogenes, Salmonella typhimurium, Shigella sonnei* and *Haemophilus influenzae.*

A number of class I enzymes are also inhibited, for example those produced by strains of *Bacteroides fragilis, Proteus vulgaris, Proteus morganii, Proteus rettgeri, Enterobacter cloacae, Citrobacter freundii,* Providencia species and *Hafnia alvei.* Thus clavulanic acid and its salts have the ability to protect β-lactamase susceptible β-lactam antibiotics from β-lactamase hydrolysis.

Clavulanic acid and its salts are of interest for use in conjunction with β-lactam antibiotics which show susceptibility to β-lactamases from both gram-positive and gram-negative organisms.

It is generally preferred to use clavulanic acid salts, having a purity of at least 98%, i.e. containing less than 2% impurities or isomers arising from production other than solvents, in conjunction with a broad spectrum β-lactam antibiotic.

In general, clavulanic acid and its salts may be used in combination with β-lactam antibiotics which are normally administered by either the oral or parenteral route. Examples of orally absorbed broad spectrum β-lactam antibiotics include cephalexin, cephaloglycin, ampicillin and amoxycillin and their orally absorbed esters, e.g. the acyloxymethyl and phthalidyl esters, and the orally absorbed esters of carbenicillin and ticarcillin e.g. the indanyl and phenyl esters. Broad spectrum β-lactam antibiotics which are not orally absorbed include carbenicillin, ticarcillin, cephalothin, cephaloridine, cefazolin, cephacetrile and cephapirin. Examples of narrow spectrum β-lactam antibiotics are penicillin G and penicillin V.

Combinations of clavulanic acid and its salts with for example penicillin G, penicillin V, ampicillin, amoxycillin, carbenicillin, cephaloridine or ticarcillin have shown synergistic activity against β-lactamase producing strains of *Staphylococcus aureus*.

Combinations of clavulanic acid and its salts with, for example penicillin G, penicillin V, ampicillin, amoxycillin carbenicillin, ticarcillin, cephalexin, cephaloglycin, cephalothin, cephaloridine, cefazolin, cephacetrile or cephapirin show synergistic activity against β-lactamase producing strains of *Escherichia coli, Klebsiella aerogenes, Proteus mirabilis, Salmonella typhimurium, Shigella sonnei, Bacteroides fragilis Proteus morganii* and *Proteus vulgaris*.

According to a further feature of the present invention therefore, we provide pharmaceutical compositions (including veterinary compositions) containing clavulanic acid, or more preferably a pharmacologically acceptable salt thereof, e.g. the sodium salt said acid and/or salt containing less than 2% impurities or isomers deriving from production other than solvents. In view of the protective action described above the compositions can advantageously contain further β-lactam antibiotics. The compositions will normally also contain a pharmaceutical (including veterinary) carrier or excipient.

The composition may be formulated for oral, parenteral, rectal or topical administration.

The compositions may, for example, take the form of powders, tablets, capsules, lozenges, solutions and syrups suitable for oral administration, and may include, for example, starch, lactose, talc, magnesium stearate, gelatin, distilled water and suspending, dispersing, emulsifying flavouring or colouring agents.

Clavulanic acid and its salts may also be formulated for parenteral administration, this mode of administration being preferred. The compounds may thus be formulated in ampoules for reconstitution before use, optionally together with a further β-lactam antibiotic compound.

In general, the weight ratio of clavulanic acid or its salt to a β-lactam antibiotic to be protected will be in the range 10:1 to 1:10, more preferably 5:1 to 1:5, especially 2:1 to 1:2.

According to a still further feature of the invention we provide a method of combatting infections caused by gram-positive and/or gram-negative organisms whereby an effective quantity of clavulanic acid or, more preferably a pharmacologically acceptable salt thereof, said acid and/or salt containing less than 2% impurities of isomers deriving from production other than solvents, is administered to a human or animal subject either prophylactically or therapeutically.

In general, the active material will be administered in conjunction with a further β-lactam antibiotic for the reasons explained above.

The clavulanic acid and/or salt may be administered to adults at a dosage level of 100 mg, to 6 g, given 2–4 times daily. Where the composition contains a further β-lactam antibiotic, the above quantities apply to the total amount of β-lactam antibiotic present. The preferred dose of clavulanic acid and/or salt thereof administered alone or with a further β-lactam antibiotic is 250 mg to 1 g, given 2–4 times daily.

A further utility of clavulanic acid and its salts is in the production of derivatives such as esters, for example, by reaction of the acid with a diazoalkane such as diazomethane or a salt of the acid with an alkyl halide e.g. methyl iodide.

PURIFICATION OF CLAVULANIC ACID AND ITS SALTS

Clavulanic acid and its salts may be isolated from a fermentation broth, prepared by culture, in accordance with British Patent Specification No. 1,315,177, of a strain of *Streptomyces clavuligerus* e.g. strain NRRL 3585 or a mutant thereof, isolation being effected using fractionation techniques to remove unwanted components of the broth such as proteins and enzymes and, in particular, other β-lactam antibiotics. However, such purification is difficult using conventional techniques, particularly due to the similar behaviour of the various β-lactam carboxylic acids present, such as Antibiotics A 16886 I and II referred to above. We have found that isolation of the antibiotic is greatly facilitated by conversion of the clavulanic acid or one of its salts into lithium clavulanate and precipitation of the latter, normally in crystalline form. Such precipitation can be effected, possibly due to surprisingly high affinity of clavulanate ions for lithium ions, with little or no significant co-precipitation of impurities, especially other β-lactams. Furthermore, by direct isolation of a salt, avoiding conversion of clavulanic acid to organic derivatives such as esters with subsequent reconversion to the acid e.g. by reductive techniques, rearrangement of clavulanic acid to isomers can be avoided. We have observed that reductive cleavage of esters of clavulanic acid can produce as much as 15% of isomeric material.

It should be noted that in fermentation broths and other solutions at approximatly neutral pH, clavulanic acid and salts formed with one or more cations will exist in equilibrium and isolation procedures will frequently be effected on clavulanic acid and/or salts thereof depending on the pH and other conditions. In general, clavulanic acid and its salts are rather unstable in aqueous solution outside the pH range 5.5 to 8 and during the procedure described below it is desirable to maintain the pH within this range, and preferably close to about pH 6.5, unless otherwise stated.

According to a further feature of the present invention therefore we provide a process for the removal of contaminating impurities from clavulanic acid of formula I, and/or salt thereof, whereby said acid and/or salt is reacted with an aqueous ionic lithium compound to yield an aqueous solution containing lithium clavulanate which is then precipitated therefrom and the precipitate separated from said aqueous solution.

In general the ionic lithium compound is a salt. Lithium chloride is preferred but lithium bromide, iodide or sulphate or lithium carboxylates such as the acetate, propionate, formate, benzoate or lactate, are also suitable. The choice of salt may be influenced by the other materials present and, for example, where the clavulanic acid salt initially present is the barium salt, lithium sulphate may be preferred to effect preliminary precipitation of barium sulphate prior to precipitation of lithium clavulanate.

In general it is preferred that the concentration of lithium clavulanate prior to precipitation is at least 0.1% by weight advantagously at least 2%, and higher concentrations, for example up to 12% or even up to 20% by weight, naturally give greater percentage recoveries.

The salt of clavulanic acid present initially, and which requires purification, may for example be an alkali metal salt (such as the sodium or potassium salt or even the lithium salt if this is present as a minor component of the clavulanic acid material), an alkaline earth metal salt (e.g. the calcium, barium or mganesium salt) or an organic base salt as described above or a salt formed with a basic ion exchange resin.

The finding that lithium clavulanate precipitates readily in a high state of purity can be made use of in a number of ways.

SALTING OUT LITHIUM CLAVULANATE

According to one embodiment of the process, the aqueous solution containing lithium clavulanate can also contain a sufficient quantity of an ionic lithium compound, usually the lithium salt used to form the lithium clavulanate, to salt out the latter by raising the concentration of lithium ions so that the solubility product of lithium clavulanate at the temperature concerned is greatly exceeded. Since the clavulanate is less soluble at lower temperatures it is normally convenient to reduce the temperature of the solution to maximise precipitation, for example to about 0°–5° C.

For such salting out, the concentration of the ionic lithium compound in the aqueous solution containing the lithium clavulanate is preferably in the range 4 M to 10 M, although concentrations up to saturation are usable; a more preferred range is 5 M to 8 M.

It may be advantageous, after harvesting a first crop of lithium clavulanate, to concentrate further and harvest a second crop.

CONVERSION OF OTHER CLAVULANATES TO LITHIUM CLAVULANATE

The solution containing lithium clavulanate may be formed simply by dissolving a salt of clavulanic acid other than the lithium salt, for example a sodium, potassium, magnesium, barium, calcium, or ammonium salt, in an aqueous solution and including therein a water soluble lithium salt such as lithium chloride. In the case of the barium salt, the use of a high concentration of lithium chloride may result in some co-precipitation of barium chloride with the lithium clavulanate. The barium chloride can, however, readily be eliminated by redissolution of the mixture in water and addition of lithium sulphate to precipitate barium sulphate, which may be removed, e.g. by filtration, followed by addition of lithium chloride to precipitate pure lithium clavulanate.

FORMATION OF LITHIUM CLAVULANATE ON AN ION EXCHANGE RESIN

According to a particularly useful application of the invention the salt of clavulanic acid used initially is a salt with a basic ion exchange resin and this is contacted with an aqueous solution of a lithium salt to yield an aqueous solution of lithium clavulanate. The resin will normally be used in the form of a column onto which impure clavulanic acid and/or a salt thereof is loaded and from which an aqueous solution of lithium clavulanate is eluted using an aqueous solution of a water-soluble lithium salt e.g. lithium chloride. The resin will normally be washed, e.g. with water, prior to elution.

The resin will generally carry amino or tertiary amino groups (weakly basic) or quaternary ammonium groups (strongly basic). The resin may, for example, be a polystyrene, polyacrylic, epoxy-polyamine, phenolic-polyamine or cross-linked dextran resin and may be macroreticular or microreticular.

The term 'resin' is used herein for convenience also to include cellulosic derivatives and the above dextran derivatives which are derived from naturally occurring polymers. Typical weakly basic ion exchange resins include Amberlite IRA68 (Microreticular: polyacrylate cross-linked with divinylbenzene: tertiary amino groups), Amberlite IRA93 (Macroreticular: polystyrene cross-linked with divinylbenzene: tertiary amino groups) all sold by Rohm & Haas (U.K.) Ltd. Typical strongly basic ion exchange resins include Zerolit FF and Zerolit FF (ip) (Sold by Zerolit Co. Ltd).

Basic ion exchange resins are advantageously in salt form when contacted with the impure clavulanic acid and/or salt; the anion is preferably the same as that of the lithium salt used as eluant, conveniently the chloride ion, but different anions may be used without significant adverse effects.

The concentration of the aqueous lithium salt used as eluant is preferably in the range 0.02 M to 8 M, the lower concentrations, however, giving very dilute solutions of lithium clavulanate and rendering subsequent precipitation more difficult. In general concentrations in the range 0.5 to 2.5 M are preferred.

Whereas adsorption/elution techniques are conventionally carried out in such a way that the desired product is subjected to a chromatographic type of separation from other adsorbed material, we have found that the subsequent step of precipitation is so effective in separating lithium clavulanate from unwanted impurities, that it is usually preferable substantially to strip the column using relatively high concentrations of lithium salt in the eluant. This gives a narrow band of clavulanate on the column which may be eluted into a relatively small volume of eluate, thus facilitating subsequent precipitation.

The eluate will normally contain the lithium salt, e.g. lithium chloride, at a concentration in the range 0.5 to 2.5 M whereas, as indicated above, the salting out effect is most efficient at concentrations in the range 5 M to 10 M. It is therefore preferred to concentrate the eluate, for example by evaporation in vacuo, e.g. by a factor of about 5. The solubility of lithium clavulanate at about 20° C. in various concentrations of aqueous lithium chloride is given in the following table:

TABLE 1

| Molarity of LiCl | Solubility in mg/ml of lithium clavulanate (approximate) |
| --- | --- |
| 2.5 | 23.5 |
| 3.75 | 10.2 |
| 5.0 | 4.1 |
| 6.25 | 1.8 |
| 7.5 | 0.8 |

The above step of concentration is preferable to addition of further lithium salt since the lithium clavulanate is also concentrated and losses in the mother liquor are thus minimised.

In order to minimise elution of adsorbed impurities from the resin, it may be advantageous to include in the eluant a water-miscible organic solvent at high concentration. Alternatively, after elution in the absence of such a solvent, this can be added to the eluate to precipitate eluted impurities and the precipitate separated off before further treatment. The solvent may, for example, be a ketone such as acetone, an alcohol such as methanol, ethanol, isopropyl alcohol or ethylene glycol, an ether such as dioxan or tetrahydrofuran or a substituted amide, imide or sulphoxide solvent such as dimethylformamide or dimethyl sulphoxide. In general, alcohols are preferred as such solvents, e.g. ethanol or isopropyl alcohol.

For such separation from unwanted impurities, the preferred concentration of alcohol in the eluant or the eluate after addition of alcohol thereto is 70 to 97% by volume.

PRECIPITATION OF LITHIUM CLAVULANATE USING A WATER-MISCIBLE SOLVENT

It should be noted that if the concentration of water-miscible organic solvent and lithium salts in the foregoing procedure is too high, the lithium clavulanate may be precipitated prematurely. It is in fact possible to precipitate lithium clavulanate from an aqueous solution by using very high concentrations of such solvents, thereby providing an alternative procedure taking advantage of the benefits of selective precipitation of lithium clavulanate outlined above. Thus, clavulanic acid and/or a salt thereof may be contacted with a lithium salt at relatively low concentration, either by elution from a column or by dissolving the salts in a single solution, and the desired precipitation effected without concentration by addition of water-miscible solvent. Thus, for example, concentrations of alcohol of at least 90% by volume, preferably at least 95%, are effective for precipitation of lithium clavulanate. It may be necessary to harvest a first crop of lithium clavulanate and then concentrate in vacuo, e.g. about four-fold, to obtain a second crop.

PREPARATION OF SALT OF CLAVULANIC ACID WITH ION EXCHANGE RESIN

The basic ion exchange resin referred to above may be loaded with the clavulanic acid and/or salt, by direct application of a fermentation broth from which solid material may have previously been removed, e.g. by filtration or centrifugation. This possibility exists because of the remarkable purification effected by the subsequent lithium precipitation stage. However, it may be preferable to treat the broth, after removal of solids, with adsorbent charcoal to adsorb the clavulanic acid and/or salt this assits in separating other salts from the clavulanate and avoids unduly loading the basic ion exchange resin with unwanted ionic material.

In general, the clarified broth may be passed through a charcoal bed, e.g. in a column, preferably using just sufficient charcoal to adsorb all the desired clavulanic acid and/or salt, usually at a ratio of about 1 part by volume of charcoal to 3–10 parts by volume of clarified broth. Ordinary charcoal is suitable and there is no need to use highly activated material.

The charcoal may then be stripped with an aqueous water-miscible solvent, e.g. a ketone such as methyl ethyl ketone, methyl isobutyl ketone or, preferably, acetone, advantageously at a concentration of from 30% to 95% ketone, preferably 50 to 70%. Before stripping, the charcoal is preferably washed, e.g. with water, to remove residual broth components.

Another variation of the above procedure is to prepare a resin salt of clavulanic acid, as described above, and to elute this with a salt other than a lithium salt, e.g. a sodium, potassium, magnesium or calcium salt, for example a chloride or acetate, or an ammonium or pyridinium salt, e.g. ammonium formate or acetate or pyridine hydrochloride, to yield an aqueous solution of the corresponding clavulanate: an excess of a water soluble lithium salt may then be added to the eluate and lithium clavulanate precipitated as previously described.

PERMENTATION OF STREPTOMYCES CLAVULIGERUS

The production of clavulanic acid from *Streptomyces clavuligerus* may be effected by conventional means, i.e. by cultivating the *Streptomyces clavuligerus* in the presence of assimilable sources of carbon, nitrogen and mineral salts. Cultivation will preferably be carried out by submerged culture under aerobic conditions.

Assimilable sources of carbon, nitrogen and minerals may be provided by either simple or complex nutrients. Sources of carbon will generally include glucose, starch, glycerol, molasses, dextrin, lactose or sucrose. Sources of nitrogen will generally include soyabean meal, corn steep liquors, distillers solubles, yeast extracts, cottonseed meal, peptones, casein or amino acid mixtures. Urea and other amides may also be used.

Nutrient mineral salts which may be incorporated into the culture medium include the generally used salts capable of yielding sodium, potassium, ammonium, iron, magnesium, zinc, nickel, cobalt, manganese, calcium, phosphate, sulphate, chloride and carbonate ions.

An antifoam will generally be present to control excessive foaming and may be added at intervals as required.

Cultivation of the *Streptomyces clavuligerus* will generally be effected at a temperature of from 20°–37° C., preferably of from 25°–30° C., and will desirably take place with agitation e.g. by shaking, or else by stirring, and aeration. The growth medium may initially be inoculated with a small quantity of sporulated suspension of the microorganism but in order to avoid a growth lag a vegetative inoculum of the organism may be prepared by inoculating a small quantity of culture medium with the spore form of the organism, and the vegetative inoculum obtained may be transferred to the fermentation medium, or, more preferably to a seed stage where further growth takes place before transfer to the principal fermentation medium.

The microorganism is a strain of *Streptomyces clavuligerus*. We have found strain NRRL 3585 and mutants thereof to be particularly satisfactory strains for the production of clavulanic acid.

In a preferred embodiment of the fermentation, therefore a slope of *Streptomyces clavuligerus* NRRL 3585, or a mutant thereof, may be used to inoculate a medium comprising sources of assimilable carbon e.g. sucrose or glycerol, assimilable nitrogen e.g. tryptones, or complex mixtures of assimilable carbon and nitrogen e.g. distiller's solubles and yeast extracts, and nutrient minerals. This medium may be allowed to grow for up to 3 days at from 25°–30° C. with agitation.

The developed inoculum thus formed may then be used to inoculate (in a quantity of up to about 10%) a nutrient medium containing similar sources of assimilable carbon, nitrogen and minerals. This fermentation will desirably be carried out at from 25°–30° C. for from 2–10 days with agitation and aeration at a pH in range 6.0 to 7.5.

FORMATION OF LITHIUM CLAVULANATE AND OTHER CLAVULANATES BY EXTRACTION OF A PHENOLIC SOLUTION OF CLAVULANIC ACID

According to a still further variation of the process, the aqueous solution containing lithium clavulanate may be obtained by extracting a phenolic solution of clavulanic acid with an aqueous solution of lithium hydroxide, precipitation of the lithium clavulanate then being effected as described above, preferably after removal of residual phenolic solvent by extracting the aqueous solution with a water-immiscible solvent such as ether, chloroform or carbon-tetrachloride.

The above technique may also be used to prepare salts of clavulanic acid other than the lithium salt by extracting the phenolic solution with an appropriate base, e.g. an alkaline earth metal hydroxide such as calcium or barium hydroxide. Any precipitate which forms, e.g. barium sulphate, should be removed and the salt may then be isolated, e.g. by freeze-drying. Purification by conversion to the lithium salt may then be effected as described above.

In general, the extraction of the phenolic solvent is preferably carried out in such a way as to yield an aqueous phase at a pH at about 6.5.

The phenolic extract may be produced by extraction of an aqueous eluate from a charcoal or resin adsorbate of the kind described above with a phenolic solvent, usually after concentrating the eluate, and if desired, after precipitating unwanted organic impurities by addition of one or more water-miscible organic solvents and/or removing such impurities by extraction with a water-immiscible solvent.

Thus, for example, in this type of procedure, the eluate from either charcoal or a resin is desirably concentrated by evaporation under reduced pressure. In general, handling during purification is preferably effected at a pH in the range 6.0-7.0, e.g. about 6.5, to minimise decomposition. The eluate may then be purified further by precipitation of unwanted material with a water-miscible ketone such as acetone, preferably to give a concentration of ketone of 50 to 90% by volume, advantageously about 85%. The pH at this step is preferably about 6.5 and where the aqueous liquid already contains water-miscible ketone this is preferably removed in order to facilitate pH measurement. The pH may be adjusted by addition of a base, e.g. an alkali metal hydroxide such as sodium hydroxide.

Further purification may be effected by a solvent extraction step, to remove unwanted components, e.g. by concentration and adjustment of the pH of the filtrate from the ketone precipitation to about 4 by addition of a mineral acid, such as sulphuric or hydrochloric acid, and extraction with n-butanol or a higher molecular weight liquid alcohol. Conveniently 1 to 8 volumes of solvent may be used.

After this extraction, the aqueous phase is preferably concentrated at about pH 6.5 and may be still further purified by extraction of the desired antibiotic into a phenolic solvent, e.g. phenol itself or a cresol, preferably after reducing the pH to about 4 with mineral acid. The phenolic solvent advantageously contains a base such as N,N-dimethylaniline and a water-immiscible solvent such as chloroform or carbon tetrachloride. The extraction is advantageously effected several times using about ⅔ volume of solvent for each extraction. The extracts may then be bulked and water, preferably about 1/15 of solvent volume, added to form a separate phase. The antibiotic may then be back-extracted by addition to the aqueous layer of a base, preferably an alkali metal hydroxide, eg. lithium hydroxide, or an alkaline earth metal hydroxide, e.g. barium or calcium hydroxide, to a pH of about 6.5. The aqueous layer is separated from the phenolic layer and the back extraction procedure is advantageously repeated, the aqueous extracts then being bulked. After separation of any precipitate, e.g. barium sulphate, any residual phenolic solvent may be removed from the aqueous solution by extraction with a water immiscible solvent such as ether, chloroform or carbon tetrachloride, and for recovery of the antibiotic salt the aqueous phase may be freeze dried or spray dried at pH 6.5.

Further purification may be effected by conventional techniques such as chromatography, in particular using materials such as Sephadex (sold by Pharmacia Ltd.). Thus, the antibiotic, which at this stage will normally be in the form of a salt, e.g. the barium salt, may be applied to a column of Sephadex, e.g. Sephadex G 15, and eluted with water, the fractions containing significant antibiotic activity being bulked for subsequent recovery of the salt e.g. by freeze drying.

CONVERSION OF LITHIUM CLAVULANATE INTO CLAVULANIC ACID AND OTHER SALTS

Purified lithium clavulanate prepared by the foregoing procedure may be converted into other salts by ion-exchange procedures e.g. using an ion-exchange resin. Thus, for example, the aqueous lithium salt may be applied to a cation exchange resin, e.g. Bio Rad AG50X8; (sold by Bio Rad Laboratories, Richmond, Calif.) in the cation form, the cation being that of the clavulanic acid salt which is required, e.g. sodium or potassium, followed by elution, e.g. with water.

Free clavulanic acid may be formed by acidification e.g. to a pH about 2.6 of an aqueous solution of the lithium salt, preferably of high ionic strength e.g. saturated with sodium chloride or ammonium sulphate in the presence of a water immiscible solvent for clavulanic acid, for example an ester solvent such as ethyl acetate. If necessary, the aqueous phase can be extracted with further solvent and the extracts combined. In general, any acid giving a sufficiently low pH will be suitable for acidification e.g. a mineral acid such as hydrochloric acid. The solvent may then be removed to yield the free acid, usually in the form of an oil.

The solution of the free acid in water-immiscible solvent may be used to prepare a wide range of salts by extraction with an aqueous solution of an appropriate base and isolation of the salt therefrom. It may be necessary to filter solid material from the aqueous phase before proceeding to isolate the salt.

Since the free acid is rather unstable, it should preferably be used, for example for preparation of salts or other derivatives, as soon as possible after its formation.

The following Preparations and Examples are given by way of illustration only:

Clavulanic acid contents of process liquors and solids were measured by:

1. U.V. Spectroscopy

Aqueous solutions of clavulanic acid and its salts show very low U.V. absorption at above 230 nm and for example the molar extinction coefficient $\epsilon$ at 280 nm is approximately 60. On dissolution in alkali, however, an intense U.V. absorption develops rapidly at $\lambda_{max} 259 \pm 1$ and this can be used to assay the clavulanic acid and/or its salts. For assay, solids were weighed out accurately and dissolved in dilute sodium hydroxide (0.1 M) to give a known volume of solution corresponding to about 0.01 mg/ml of clavulanic acid. The optical density of the solution at an absorption maximum at or around 259 nm was measured on a suitable spectrophotometer; solid purities may be calculated assuming $\epsilon$ for clavulanic acid to be 16,700. Molar extinction coefficients may be calculated from $E_1^1$ values, that is the extinction coefficients for a 1% solution in a 1 cm cell. Similarly, process liquors, after removal of organic solvents if necessary, were diluted accurately with dilute sodium hydroxide to give similar concentrations of alkali and clavulanic acid, whence the clavulanic acid concentration in the original liquor was determined as above. Values for crude solids and process liquors were corrected for absorption by impurities using solutions of the same concentration in water.

2. Biological Activity

Determined by comparison with solutions of solids of known clavulanic acid content in agar cupplate assay against Acinetobacter sp. essentially following the method of Lees and Tootill (Lees, K. A. & Tootill, J. P. R., Analyst, 1955, 80 (947), 95-110; ibid 110-123; 80 (952), 531-535).

All media were steam sterilised before fermentation. Temperature are in °C.:

PREPARATION 1

Preparation of Barium Salt

(a) Inoculum Development

Sterile distilled water (10 ml) was added to a 14 day old malt/yeast extract agar slope of *Streptomyces clavuligerus* NRRL 3585 and a suspension made.

A portion (1.5 ml) of this suspension was used to inoculate 150 ml of a medium containing:

|  | % (w/v) |
| --- | --- |
| sucrose | 2.0 |
| distillers' solubles | 1.5 |
| yeast extract | 0.5 |
| $K_2HPO_4$ | 0.02 |
| tryptone | 0.5 |
| glycerol | 1.0 | and water to 100% in a 2 liter florence flask.

This flask was incubated at 26° C. for 48 h at 220 rev./min. on a rotary shaker with a 2 inch throw. 150 ml of this inoculum were used to inoculate 4 l of a medium containing:

|  | % (w/v) |
| --- | --- |
| soya bean meal | 2.1 |
| distillers' solubles | 0.52 |
| casein hydrolysate | 0.52 |
| $FeSO_4.7H_2O$ | 0.01 |
| soluble starch | 4.7 |
| glucose | 0.78 | and water to 100% in a 5 liter fermenter with aeration (0.75 vol/vol/min) and kept at 28° C. with stirring (750 rev/min) for 20 h.

(b) Fermentation 7.5 l of the 20 h inoculum of (a) were inoculated into 150 l of a medium containing

|  | % (w/v) |
| --- | --- |
| soluble starch | 4.7 |
| soya bean meal | 2.1 |
| distillers' solubles | 0.52 |
| casein hydrolysate | 0.52 |
| glucose | 0.78 |

-continued

|  | % (w/v) |
| --- | --- |
| $FeSO_4.7H_2O$ | 0.01 |
| polyglycol (P.2000: Dow Chemical Co.) | 0.05 | and water to 100% in a 200 liter vessel and fermented for 90 h at 28° C. with aeration (2 vol/vol/min) and agitation (350 rev/min).

(c) Isolation

The whole broth from step (b) was adjusted to pH 6.3 and clarified by centrifugation. The clear supernatant (89 l) was applied to a column containing Pittsburgh CAL charcoal (20 l).

The charcoal was washed with distilled water (40 l) and then drained as dry as possible. The charcoal was eluted, with acetone (10 l) followed by 90% aqueous acetone (40 l). Eluate fractions (5×10 l) were collected and each fraction was evaporated under reduced pressure to remove acetone.

Fraction 1 (5 l aqueous solution) was concentrated by freeze drying to 2.2 l and acetone added to give a final concentration of about 84% acetone. To fraction 2 (0.5 l aqueous solution) was added acetone to give a final concentration of about 84% acetone. Fractions 1 and 2 were then each filtered through filter-aid (Celite 535), the filtrates evaporated under reduced pressure to remove acetone and the resultant aqueous solutions combined.

The aqueous solutions of fractions 3 to 5 were combined and freeze-dried to give a solid. The aqueous solution of combined fractions 1 and 2 was then added to the solid of combined fractions 3 to 5 to give a solution that was concentrated by freeze-drying to 0.76 l. This solution (pH 4) was immediately extracted with butan-1-ol (1×1.52 l, 5×380 ml).

The aqueous phase after removal of butanol by evaporation under reduced pressure was brought to pH 4.2 (from 5.6) with sulphuric acid and extracted with an equal volume of 72% aqueous phenol/N,N-dimethylaniline/carbon tetrachloride (53:5:15 by vol.). The solvent layer was then extracted with aqueous barium hydroxide (500 ml) to give an aqueous solution of pH 6.5. Suspended barium sulphate was removed by filtration and the filtrate was washed with diethyl ether and freeze dried to give 11.1 g solid barium salt. $E_1^1$ 220.

PREPARATION 2

Preparation of Barium Salt

A fermentation broth obtained by a method similar to that of Preparation 1 (a) and (b) was purified as follows: Fermentation broth (135 l) at pH 6.25 was clarified on a centrifuge to give supernatant (112 l) at pH 6.3. This was passed through a column of Pittsburgh CAL charcoal (25 l), and the column washed through with water (50 l). Acetone (10 l) was poured gently onto the top of the bed and elution started. This was followed by 90% aqueous acetone (60 l). The eluate was collected in fractions (1×10 l, 2×25 l).

Each fraction was distilled under reduced pressure to remove acetone. The residual aqueous solution was adjusted to pH 6.0 with 1 M sodium hydroxide. The fractions were then bulked and further distilled to 2.9 l, transferred to a suitable container and with boiler washings made up to 3.3 l. Acetone (17 l) and Celite 535 (500 g) were added to the concentrate with vigorous stirring.

The resulting suspension was filtered and the cake washed with 85% aqueous acetone (4 l).

The combined filtrate and washings were distilled under reduced pressure to 4.0 l. The pH was adjusted from 5.65 to 6.0 with 1 M sodium hydroxide and distillation continued until the volume was 1.0 l. The resulting concentrate was acidified to pH 4.0 with 20% sulphuric acid and washed with butan-1-ol (4×750 ml, 1×500 ml). Dissolved butan-1-ol was distilled out of the aqueous phase under vacuum.

After being adjusted to pH 4.2 with 20% sulphuric acid the concentrate was extracted 3 times with a mixture of liquified phenol B.P. (265 ml), carbon tetrachloride (75 ml) and N,N-dimethylaniline (25 ml). The pH was adjusted to 4.2 for each extract. The combined solvent extracts were stirred with water (250 ml) and the pH adjusted to 6.5 with saturated aqueous barium hydroxide (70 ml). After separation of the phases the solvent was re-extracted with water (200 ml) and saturated aqueous barium hydroxide (7 ml).

The combined aqueous phases were washed with diethyl ether (3×200 ml), reduced in vacuum to 200 ml and freeze-dried to yield 29.4 g pale brown solid. $E_1^1 = 152$.

PREPARATION 3

Preparation of Charcoal Eluate Containing Clavulanic Acid (a) Inoculum Development Sterile distilled water (10 ml) was added to a 14 day old malt/yeast extract agar slope of *Streptomyces clavuligerus* NRRL 3585 and a suspension made.

A portion (2.0 ml) of this suspension was used to inoculate 150 ml of a medium containing:

|  | % (w/v) |
|---|---|
| sucrose | 2.0 |
| distillers solubles | 1.5 |
| yeast extract | 0.5 |
| K$_2$HPO$_4$ | 0.02 |
| tryptone | 0.5 |
| glycerol | 1.0 |
| and water to 100% | | in a 2 liter florence flask.

The flask was incubated at 26° C. for 48 h on a rotary shaker (5 cm throw; 220 rev./min.).

The contents of six such flasks (900 ml total) were used to inoculate six 5-liter fermenters each containing 4.5 l of a medium containing:

|  | % (w/v) |
|---|---|
| soya meal | 2.1 |
| distillers solubles | 0.52 |
| casein hydrolysate | 0.52 |
| ferrous sulphate heptahydrate | 0.01 |
| soluble starch | 4.7 |
| glucose | 0.78 |
| silicone antifoam emulsion | 0.05 (v/v) |
| and water to 100% | |

The fermenters were aerated (0.67 vol/vol/min) and agitated (750 rev./min; two impellers 7.5 cm diameter) for 20 h at 28° C.

(b) Fermentation

Inoculum (25 l) from the 5 l fermenter stage was used to inoculate 475 l of a medium containing:

|  | % (w/v) |
|---|---|
| soya meal | 3.0 |
| ferrous sulphate heptahydrate | 0.01 |
| K$_2$HPO$_4$ | 0.01 |
| soluble starch | 4.7 |
| silicone antifoam emulsion | 0.05 (v/v) |
| and water to 100% | | contained in a 700 l, stainless steel fermenter agitated at 350 rev./min (25 cm diameter impeller and four 7.5 cm baffles) and aerated at 0.56 vol/vol/min. The fermentation was carried out at 28° C. for 92 h and extra antifoam was added as necessary. The fermentation was maintained at pH 6.5.

(c) Isolation

The whole broth from step (b) was adjusted to pH 5.45 with strong sulphuric acid and filtered on a rotary drum filter with a cellulose precoat. The filtrate (430 l) containing the antibiotic was adsorbed onto charcoal (Pittsburgh CAL; 135 l) in columns. The charcoal was washed with water (90 l) to displace the filtered broth, and the antibiotic was eluted with aqueous acetone (60% v/v; 180 l).

EXAMPLE 1

(i) Preparation of Calcium Salt (a) Crude barium salt from Preparation 2 (8.83 g) was added to 50 ml of a saturated aqueous solution of (NH$_4$)$_2$SO$_4$. Ethyl acetate (50 ml) was added and the mixture stirred. A pH probe was inserted into the mixture and the pH was adjusted from pH 6.8 to pH 2.6 with about 15 ml 1 M H$_2$SO$_4$. The aqueous solution was separated from the ethyl acetate and stirred again with a fresh portion of ethyl acetate (50 ml). The two ethyl acetate extracts were combined, distilled water (100 ml) added and the mixture stirred in the presence of the pH probe. About 40 ml of a saturated solution of calcium hydroxide were added to bring the pH of the mixture to 6.6. The aqueous solution was separated from the ethyl acetate, filtered through filter-aid and freeze-dried to give 1.44 g of solid calcium salt.

(b) The solid from (a) was dissolved in 15 ml distilled water, filtered through a Millipore filter and applied to a column containing Sephadex G15, packed in water to give a bed of height 60 inches and diameter 1 inch. Elution was with distilled water and 20 ml fractions were collected. The fractions were assayed after TLC (cellulose, Eastman-Kodak 6065 plates; solvent, acetonitrile-water, 7:3 by vol.) by overlay with nutrient agar containing *Staphylococcus aureus*. Fractions 33–37 were combined and freeze-dried to give 490 mg. The solid was kept over P$_2$O$_5$ in vacuo for 60 h. The calcium salt from (b) had the following characteristics:

pKa

The pKa value of the corresponding acid was found to be about 2.4 by potentiometric titration of the salt.

Optical rotation $[\alpha]_D$ at 22° C., +44.9° (concn., 0.287 g/100 ml water).

UV Spectrum

A sample (0.00148 g) that had been dissolved in 100 ml of 0.1 M NaOH showed an absorption maximum ($\lambda$max) at 258 nm with an $E_1^1$ value of about 550.

IR Spectrum

The infrared spectrum of a Nujol mull of the sample showed absorption maxima at wave numbers (cm$^{-1}$).

| | | | |
|---|---|---|---|
| 3300 s,br | 2330 w | 1788 s | 1692 m |
| 1604 s | 1404 s | 1305 s | 1190 m |
| 1118 m | 1082 m | 1060 m | 1042 m |
| 1012 m | 992 m | 968 m | 892 m |
| 848 w | 790 w | 740 m | 654 w |

(s, m, br and w = strong, medium, broad and weak intensity respectively)

The full spectrum is shown in FIG. 3 of the accompanying drawings.

N.M.R. Spectrum

The proton n.m.r. spectrum of a solution of the sample in heavy water showed groups of peaks ($\tau$ values) centered at about 4.31, 5.10, 5.85, 6.46, 6.91.

Thin layer chromatography

Portions of the sample, dissolved in water, were applied to the origin of either Eastman-Kodak cellulose TL plates (plastic-backed, EK 6065) or Eastman-Kodak silica TL plates (plastic-backed, Ek 6060). Plates were developed with solvent at room temperature, then air-dried and overlaid with nutrient agar containing *Staphylococcus aureus*. Rf values, calculated as the distance from the origin to the centre of each zone of inhibited bacterial growth divided by the distance from the origin to the solvent front, are given below for five systems.

| Solvent | Support | Rf |
|---|---|---|
| Propan-1-ol:water (7:3) | Cellulose | 0.60 |
| Butan-1-ol:acetic acid:water (3:1:1) | " | 0.64 |
| Acetonitrile:water (7:3) | " | 0.68 |
| Acetonitrile:water:propan-2-ol (1:1:1) | " | 0.87 |
| Butanol-1-ol:acetic acid:water (3:1:1) | Silica | 0.63 |

Paper ionophoresis

Portions of sample were subjected to ionophoresis on Whatman 541 paper for 1 h with 400 V applied over 20 cm. Activity, detected by overlay of the air-dried paper with nutrient agar containing *Staphylococcus aureus*, had a mobility, relative to cyanocobalamin, of 4.5 cm towards the anode at pH 4.8 (0.01 M acetate), pH 6.9 (0.01 M phosphate) and pH 9.5 (0.01 M pyrophosphate).

(ii) Preparation of Lithium Salt

Calcium salt (1 g; ($E_1^1$ 590) pure by u.v. assay) prepared as in (i)(b) above was dissolved in 10 ml water and 10 ml of a saturated solution of lithium chloride in water was added. Crystallisation occurred without scratching or seeding. After cooling to 0° the crystals were filtered, washed with 5 ml ethanol, 5 ml acetone and 2×5 ml diethyl ether. The crystals were dried under reduced pressure (0.1 mm Hg) over silica gel for 2 hours to give 495.5 mg solid lithium salt. This salt had the following characteristics:

Elemental analysis

Found (mean values are given within brackets): C, 45.5, 45.8 (45.65); H, 3.8, 3.8 (3.8); N, 7.0, 7.2 (7.1); Li, 3.2%. Sulphur not detected by a method given by N. D. Cheronis & J. B. Entrikin (1947) in Semimicro Qualitative Analysis, p. 93. Crowell, New York. $C_8H_8NO_5$·Li·$\frac{1}{4}H_2O$ requires, C, 45.84; H, 4.06; N, 6.68; Li, 3.31%.

The Li analysis value quoted above, (3.2%) was determined by atomic absorption spectrophotometry. Sulphated ash was 26.8% which calculated as $Li_2SO_4$ is equivalent to 3.38% lithium.

pKa

The pKa value of the corresponding acid was found to be about 2.3 by potentiometric titration of the salt.

Optical rotation

The $[\alpha]_D$ value for a 0.145% w/v aqueous solution at 24° was +66.0°.

Ultraviolet spectrum

The u.v. absorption spectrum of a 0.00091% solution in 0.1 M sodium hydroxide had an absorption maximum ($\lambda$max) at 258 nm with an $E_1^1$ value of 788 which calculates to a molar extinction coefficient of 16510.

Infrared spectrum

The i.r. spectrum of a Nujol mull showed absorption peaks (cm$^{-1}$) at about:

| | | | | |
|---|---|---|---|---|
| 3420 (m) | 1402 (s) | 1200 (w) | 1026 (m) | 880 (w) |
| 3012 (w) | 1338 (m) | 1129 (m) | 992 (m) | 850 (w) |
| 1765 (s) | 1325 (s) | 1101 (m) | 976 (m) | 734 (m) |
| 1683 (s) | 1300 (m) | 1062 (m) | 950 (s) | 708 (w) |
| 1618 (s) | 1224 (w) | 1048 (s) | 900 (m) | |

The full spectrum is shown in FIG. 1 of the accompanying drawings.

N.M.R. Spectrum

A 100 MHz proton n.m.r. spectrum of the lithium salt in heavy water solution showed peaks [$\tau$ values with multiplicities and coupling constants (Hz) in parentheses] centred at about 4.26 (d,3), 5.05 (t,8), 5.06 (s), 5.81 (d,8), 6.43 (dd, 3 and 17) and 6.89 (d,17). (s, d, dd, t and m = singlet, doublet, double-doublet, triplet and multiplet respectively).

EXAMPLE 2

Recrystallization of Lithium Salt

Lithium salt (0.1 g) prepared in Example 1 (ii) was dissolved in water (1.0 ml) and carefully diluted with isopropanol (19 ml). The product crystallized slowly at 0° and was harvested in two crops by boiling down under reduced pressure to 5 ml for second crop. The crystals of lithium salt were dried over silica gel in vacuo for 3 days.

Crop 1. 20.0 mg, $\lambda_{max}$ 259 nm. $E_1^1$=814 in sodium hydroxide solution (0.1 M) at 10 $\mu$g/ml.

Elemental analysis found: C=46.2, 46.0; H=4.10, 3.85; N=6.8, 6.7%. $C_8H_8NO_5Li\frac{1}{4}H_2O$ requires C=45.84; H=4.06; N=6.68%.

Crop 2. 67.0 mg. $\lambda_{max}$259 nm. $E_1^1$=800 in sodium hydroxide (0.1 N) at 10 $\mu$g/ml.

Elemental analysis found C=46.15, 46.5; H=3.9, 4.0; N=6.65, 6.5 lithium 3.4% (sulphated ash). $C_8H_8NO_5$·Li·$\frac{1}{4}H_2O$ requires: C=45.84; H=4.06; N=6.68; Li=3.31%.

EXAMPLE 3

Barium salt (30 g; $E_1^1$ 274 prepared as in Preparation 2 was dissolved in water (40 ml) and saturated ammonium sulphate solution (300 ml) added. The pH of the solution was adjusted to 2.3 with sulphuric acid (20%, 23.0 ml) and then extracted with ethyl acetate (2×300 ml). Water (200 ml) was added to the combined extracts. The mixture was stirred vigourously and sodium hydroxide solution (1 M; 39.3 ml) added until the pH reached 6.8. The aqueous phase was separated and distilled under reduced pressure to 33 ml. Butan-1-ol (770 ml) was added to the aqueous concentrate and then mixed, warmed to 40° C. and shaken vigorously. Insoluble material was filtered off and re-extracted with water: butan-1-ol (1:23 v/v) until all dissolved. The combined solutions were cooled to 4° C. overnight. The crystalline solid formed was collected by filtration, washed with butan-1-ol and acetone, and air dried to give 3.34 g of sodium salt ($E_1^1$ 648).

2.92 g of this sodium salt were dissolved in water (20 ml) and filtered. The filtrate was stirred at 0° whilst lithium chloride solution (20 ml, saturated at 20°) was introduced over 5 min. The stirring and cooling were continued for 1 h after which the crystals were harvested by filtration, washed with ethanol (20 ml), acetone (2×20 ml), diethyl ether (2×25 ml) and air dried to give the lithium salt (2.275 g) as white elongated flat prisms ($E_1^1$ 770).

EXAMPLE 4

Crude barium salt (7.99 g; $E_1^1$ 288) prepared as described in Preparation 2 was dissolved in water (60 ml) and filtered. The filtrate was treated portionwise with lithium sulphate (4.0 g) with stirring at ambient temperature until no test was given for barium on an external spotting plate with sodium rhodizonate. The suspension was clarified by centrifugation, and the supernatant decanted and boiled down to approx. 35 ml under reduced pressure. Lithium chloride (9.0 g) was added in portions with stirring and cooling; after 1 h at 0° the lithium salt was harvested by fitration, washed with ethanol (10 ml), acetone (2×25 ml), diethyl ether (2×20 ml) and air-dried in the filter funnel to give 1.590 g of white prisms ($E_1^1$ 790).

EXAMPLE 5

Preparation of Sodium Salt

Lithium salt prepared as in Example 1(ii) (3.5 g) was dissolved in 20 ml distilled water and applied to a column containing 50 ml AG50×8 cation exchange resin (Bio-Rad, Na+; 200–400 mesh size). Elution was with water and 8 ml fractions were collected. The fractions were assayed, after application of portions to paper, by overlay with nutrient agar containing *Staphylococcus aureus*. Active fractions (4 to 13) were combined and freeze-dried.

Freeze-dried solid was dissolved in distilled water to give 19 ml of solution, shaken with butan-1-ol (450 ml) and warmed (water bath) until the solution was almost clear. The warm solution was filtered through a sinter to remove yellow solid and the filtrate kept at 4° C. for 60 hours. Crystals that formed were filtered, washed with butan-1-ol (2×10 ml) then acetone (2×10 ml) and dried under reduced pressure at 40° C. for 1 hour to give 2.18 g solid. The solid was recrystallised from water-butan-1-ol (1:23.3 by vol.) as described. The crystals were dried under reduced pressure over silica gel at 44° C. for 1.5 hours to give 1.8 g solid sodium salt.

The solid was hygroscopic. It was ground in a pestle and mortar and allowed to take up atmospheric water at 18° C. After about 22% (w/w) of water was taken up, an equilibrium was reached.

This salt had the following characteristics:

Elemental analysis (of equilibrated moist solid): Found (mean values are given within brackets): C, 33.3, 33.2 (33.25); H, 4.6, 4.6 (4.6); N, 4.6, 4.7 (4.65); Na, 7.3 (by absorption spectrophotometry), 7.9 (calc. from sulphated ash); water, 21.95%. $C_8H_8O_5N$ Na.4H$_2$O requires C, 32.76; H, 5.46; N, 4.78; Na, 7.8; water, 24.57%.

Metal analysis (1) Found by atomic absorption spectrophotometry: Na 7.3±0.2% (This value is quoted under elemental analysis)

(2) Assuming that sulphated ash is Na$_2$SO$_4$, the Na content was calculated as 7.9%.

Optical rotation

The $[\alpha]_D$ value for a 0.134% (w/v) aqueous solution at 24° C. was +47°.

Ultraviolet spectrum

The U.V. absorption spectrum of a 0.00098% solution in 0.1 M NaOH had an absorption maximum ($\lambda$max) at 258 nm with an $E_1^1$ value of 555 which calculates to a molar extinction coefficient of 15760.

Infrared spectrum

The IR spectrum of a Nujol mull showed absorption peaks (cm$^{-1}$) at about

| | | | | | |
|---|---|---|---|---|---|
| 3400 s | 1592 s | 1288 m | 1080 w | 986 s | 850 w |
| 3300 s | 1396 s | 1206 w | 1060 m | 967 m | 802 w |
| 1792 s | 1348 m | 1190 m | 1048 m | 945 w | 753 m |
| 1690 s | 1310 s | 1138 m | 1015 s | 902 m | |
| 1665 m | 1302 sh | 1120 m | 998 m | 880 w | |

The full spectrum is shown in FIG. 2 of the accompanying drawings.

N.M.R. Spectrum

The proton n.m.r. spectrum of a solution in heavy water showed groups of peaks ($\tau$ values) centered at about 4.28, 5.07, 5.82, 6.44 and 6.88.

EXAMPLE 6

Preparation of Potassium salt

Lithium salt (3.0 g) prepared as in Example 1(ii) was dissolved in water (100 ml) and passed through a Dowex 50W×2 column (450 ml, potassium cycle). A forerun (150 ml) was discarded. The next 400 ml of eluant were collected and evaporated to 15 ml under reduced pressure. Butan-1-ol (340 ml) was added and the mixture warmed and well shaken. Some insoluble solid was filtered off. The filtrate was distilled under reduced pressure to 200 ml, then stored at 4° C. overnight. The crystalline deposit was filtered, washed with butan-1-ol (2×10 ml), acetone (2×50 ml) and diethyl ether (2×50 ml) and finally dried in a vacuum desiccator at ambient temperature. Yield 2.34 g of potassium salt. ($E_1^1$=704 which calculates to a molar extinction coefficient of 17000). The $E_1^1$ was determined by dissolving 7.1 mg of the potassium salt in 100 mls of water. This solution was diluted 1 in 10 with 0.1 M sodium hydroxide to give a final solution of 7.1 µg/ml.

Elemental Analysis

Found: (Mean values are given within brackets): C, 40.0, 40.14 (40.07); H, 3.5, 3.55 (3.53); N, 6.0, 5.82 (5.91); K (by absorption spectrophotometry) 16.0, (by sulphated ash) 15.9; water 1.75, 1.95 (1.85) % $C_8H_8NO_5K$·¼H$_2$O requires C, 39.7; H, 3.5; N, 5.8; K, 16.2, water 1.96%.

Optical Rotation

The $[\alpha]_D^{23°}$ value for a 0.276% w/v aqueous solution was +58.4°.

The calcium, barium and magnesium salts of clavulanic acid were prepared from lithium clavulanate in a similar way and were found to have $E_1^1$ values 530, 576 and 713 respectively.

EXAMPLE 7

Preparation of Free Clavulanic Acid

Lithium salt (500 mg), prepared as in Example 1(ii), was partitioned between ethyl acetate (10 ml) and saturated aqueous sodium chloride (10 ml). 2 N hydrochloric acid (1 ml) was added and the mixture shaken briefly. The aqueous phase was separated, washed with ethyl acetate (10 ml) and the combined organic extracts washed with saturated aqueous sodium chloride (15 ml). The resulting organic solution was dried over sodium sulphate and evaporated almost to dryness to afford the free acid as an oil (352 mg) containing ca. 0.5 mole of ethyl acetate. The compound had the following characteristics: $[\alpha]_D^{24}$ (c 1.0; DMSO)+54.5°, $\lambda_{max}$ of a 0.00098% solution in aqueous 0.1 N NaOH is 258 nm ($E_1^1$ 590), infrared peaks of a Nujol mull include 3350, 1790 and 1722 cm$^{-1}$, n.m.r. peaks (DMSO-d$_6$) include $\tau$ 4.31 (d, 3 Hz), 4.99 (s,), 5.23 (t, 7 Hz), 5.97 (d, 7 Hz), 6.37 and 6.93 (dd, 3 and 17 Hz; d, 17 Hz); peaks centred at $\tau$ 8.82, 8.00 and 5.95 indicated that the sample contained about 0.5 mole of ethyl acetate per mole clavulanic acid. These values indicate that the sample contained at least 85% by weight of clavulanic acid.

EXAMPLE 8

Preparation of the Ammonium Salt

A column (240 ml) of Dowex 50W was converted to the ammonium cycle by treatment with ammonium sulphate and washed free of sulphate with water. Lithium salt (1.0 g) was dissolved in water (15 ml), applied to the column and the column developed with water. Fractions were taken (25 ml) and tested for U.V. absorption in 0.1 N sodium hydroxide. Active fractions (4–7) were bulked and distilled to near dryness (2 ml) under reduced pressure and n-butanol (85 ml) added. The mixture was carefully distilled at 25° C. under 0.1 mm pressure until a crystalline material was precipitated. The ammonium salt was harvested by filtration, washed with a very little ethanol, acetone and finally washed with diethylether and dried at 0.1 mm for 6 h to give off-white crystals (0.54 g). $[\alpha]_D^{23}$ (c 0.39% in water)+60.1°; $\lambda$max (0.1 N sodium hydroxide, 8.8 µg/ml) 258 nm ($E_1^1$ 745); i.r. peaks in Nujol include 3360, 1780, 1700 and 1580 cm$^{-1}$; $\tau$ (5% D$_2$O) values include 4.27 (d, 3 Hz), 5.08(s), 5.09 (t, 7 Hz), 5.84 (d, 7 Hz), 6.43 (dd, 17 Hz, 3 Hz), and 6.89 (d, 17 Hz). Found C, 44.4; H, 5.6; N, 13.3% C$_8$H$_8$NO$_5$NH$_4$ requires C, 44.4; H, 5.6; N, 13.0%. A trace of water (0.6%) was found by Karl Fischer analysis.

EXAMPLE 9

Preparation of Methylamine Salt

A column (200 ml) of Amberlite IR 120 H$^+$ was converted to the methylammonium form by treatment with 0.5 M methylamine solution in water. This was washed to neutrality with water and methylammonium chloride (3.0 g) in water (10 ml) introduced. The column was washed free of chloride with water and was ready for use.

Lithium salt (1.50 g) was dissolved in water (15 ml) and introduced to the top of the column. The column was developed in water and fractions (25 ml) taken.

Fractions 3–7 were combined (161 ml with washings), distilled at 35°/1.0 mm to approx. 2 ml and n-butanol (200 ml) added. The clear solution was distilled under similar conditions to 20 ml when crystallization took place. The crystals were harvested by filtration after 1 h at 2°, washed with diethylether (2×15 ml) and dried for 3 hours at 1 mm to give the methylamine salt (1.2 g) as clusters of white elongated prisms. $[\alpha]_D^{23}$ (c 0.23% in water)+56.1° $\lambda$max (0.1 N sodium hydroxide, 9.5 µg/ml) 260 nm ($E_1^1$ 584); i.r. peaks in Nujol include 2500, 1790, 1692, 1632 and 1576 cm$^{-1}$; $\tau$ (8% D$_2$O) values include 6.40 and 6.86 (dd, 17 Hz, 3 Hz: d, 17 Hz), 4.24 (d, 3 Hz), 5.06 (t. 7 Hz), 5.78 (d, 7 Hz), 5.08 (s), 7.42 (s). Found C, 46.7; H, 6.1; N, 12.5%. C$_9$H$_{14}$N$_2$O$_5$ requires C, 47.0; H, 6.1 and N, 12.2%.

EXAMPLE 10

Preparation of Piperidine Salt

A column of ion-exchange resin (200 ml Bio-Rad Laboratories, AG ® 50W×2, 100–200 mesh H$^+$ form) was converted to the piperidinium form with a solution of piperidine (75 ml) in water (1500 ml). The resin was washed to neutrality with water and treated with piperidinium chloride (3 g) in water (10 ml). The column was washed free of chloride with water and was ready for use.

Lithium salt (1.50 g) was introduced at the top of the column in water (15 ml) and the column developed in water taking 25 ml fractions. Fractions 3–6 were bulked with washings (172 ml).

The solution was evaporated to near-dryness at 35°/1.0 mm and pure toluene added. The oily suspension was evaporated to dryness under reduced pressure as above and the crystalline solid so obtained triturated with ethyl acetate (90 ml). The crystalline piperidinium salt was harvested by filtration, washed with ethyl acetate (3×30 ml) and the residual solvent removed at 0.1 mm Hg for 3 h to yield 1.775 g of slightly off-white prisms. $[\alpha]_D^{24}$ (c 0.35% in water)+42.2°; $\lambda$max (0.1 N sodium hydroxide, 10 µg/ml) 259.5 nm ($E_1^1$ 474); i.r. peaks in Nujol include 3380, 2540, 1782, 1682 and 1608 cm$^{-1}$; $\tau$ (8% D$_2$O) values include 6.90 (d, 17 Hz), 6.44 (dd, 3, 17 Hz,), 4.28 (d, 3 Hz), 5.08 (s), 5.84 (d, 8 Hz), 5.08 (t, 7 Hz), 6.84 (complex multiplet), 8.0–8.5 (complex multiplet). Found C, 52.8; H, 7.2; N, 9.3%. C$_{13}$H$_{20}$N$_2$O$_5$. 0.6H$_2$O requires C, 52.9; H, 7.4; and N, 9.5%.

EXAMPLE 11

Preparation of Triethylamine Salt

A column of ion-exchange resin (Bio-Rad AG ® 50W as described in Example 10 was converted to the triethylammonium form with a solution of triethylamine in water (0.5 N, 1.5 liters) and washed to neutrality with water. A solution of triethylammonium chloride (3 g) in water (15 ml) was introduced to the column, the column was washed free of chloride with water and was ready for use.

Lithium salt (1.5 g) was introduced to the top of the column in water (15 ml) and the column developed in water taking 25 ml fractions. Fractions 4–9 were bulked (175 ml with washings).

The solution was boiled down under reduced pressure (35°/1.0 mm) to give an oil which was boiled down three times with toluene under the same conditions. The resultant crystals were broken up under ethyl acetate (50 ml), harvested by filtration, washed twice with diethyl ether (2×20 ml) and freed of residual solvent in a desiccator for 3 h at 0.1 mm to give the triethylammonium salt (1.588 g) as slightly off-white prisms. $[\alpha]_D^{25}$ (c 0.22% in water)+44.3°; $\lambda$max (0.1 N sodium hydroxide, 9.7 μg/ml) 258 nm ($E_1^1$ 485); i.r. peaks in Nujol include 3250, 2080, 1784, 1700 and 1640 cm$^{-1}$; τ (10% $D_2O$) values include 6.41 and 6.87 (dd 17 Hz, 3 Hz: d 17 Hz), 4.26 (d, 3 Hz), 5.07 (t, 7 Hz), 5.78 (d, 7 Hz), 5.07 (s), 8.74 (t, 7 Hz) and 6.78 (q, 7 Hz). Found C, 55.2; H, 7.9; N, 9.2%, $C_{14}H_{24}N_2O_5 \cdot \frac{1}{4}H_2O$ requires C 55.2; H, 8.0 and N, 9.2%.

EXAMPLE 12

A sample of charcoal eluate prepared as in Preparation 3 was concentrated under reduced pressure to remove the acetone. The resulting concentrate (1 l; containing 1.28 g clavulanic acid by bioassay) was applied to a column of IRA68 resin (chloride cycle; 100 ml). The column was washed with water (300 ml) and eluted with 5% (w/v) aqueous lithium chloride solution, collecting the eluate in fractions of 100 ml.

Fractions 1 and 2 were combined (200 ml), evaporated under reduced pressure to 40 ml and left at 4° C. overnight. The crystals formed were filtered, washed successively with ethanol (10 ml), acetone (50 ml) and diethyl ether (50 ml) before drying in vacuo to give 530 mg white solid ($E_1^1$ 802) representing a 40.8% yield from the charcoal eluate. Addition of an equal volume of saturated aqueous lithium chloride to the mother liquors followed by storage at 4° C. gave a second crop, worked up as above, of 178 mg ($E_1^1$ 740) representing a further yield of 12.7%.

In a series of similar experiments the concentration of the lithium chloride eluant, the ion-exchange resin and the nature of the eluant cation and counter anion were varied to give the results as tabulated.

| Resin | Cycle | Eluant (molarity) | $E_1^1$ | Product yield %* |
|---|---|---|---|---|
| Amberlite IRA 68 | Chloride | Lithium chloride (0.5M) | 750 | 51.8 |
| Amberlite IRA 68 | Chloride | Lithium chloride (0.25M) | 760 | 55.6 |
| Amberlite IRA 93 | Chloride | Lithium chloride (1.0M) | 560 | 50.3 |
| Amberlite IRA 93 | Chloride | Lithium chloride (0.5M) | 640 | 44.5 |
| Amberlyst A 21 | Chloride | Lithium chloride (1.0M) | 630 | 54.3 |
| Amberlite IRA 68 | Acetate φ | Lithium acetate (0.5M) | 660 | 56.8 |
| Amberlite IRA 68 | Formate φ | Ammonium formate (0.5M) | 520 | 55.8 |

*Product yield based on input charcoal eluate
φ In these experiments the lithium salt was prepared by concentration of the eluates × 6 and addition of an equal volume of 50% (w/v) lithium chloride solution. The resultant lithium salts were worked up as before.

EXAMPLE 13

A sample (4 liters) of charcoal eluate prepared as in Preparation 3 was passed down a column of IRA68 (chloride cycle; 250 ml) which was then washed with water (250 ml) and eluted with 5% (w/v) lithium chloride solution. 200 ml of the eluate containing 73% of the input biological activity were collected. A sample (70 ml) of this eluate was treated with 5 volumes of propan-2-ol with stirring, to give a tarry precipitate. The supernatant was decanted and concentrated under reduced pressure to 7 ml. After standing at 4° C. overnight the crystalline product was filtered, washed successively with ethanol, acetone and diethyl ether before drying in vacuo. The dry solid (870 mg) was estimated to be pure by biological assay, and represented a yield of 94% from the resin column eluate.

EXAMPLE 14

A column of IRA68 resin (chloride cycle; 50 ml) was charged with charcoal eluate (840 ml) prepared as in Preparation 3, washed with water (100 ml) and eluted with 5% (w/v) lithium chloride in propan-2-ol:water (5:1). The first 5 bed volumes were concentrated under reduced pressure, and the antibiotic was crystallised as in Example 13. The solid weighed 292 mg (Bioassay: 970 mg lithium clavulanate/mg solid) and represented a yield of 45% from charcoal eluate.

EXAMPLE 15

Broth was fermented and filtered as in Preparation 3, and a sample of filtered broth (1 l) containing 0.43 g clavulanic acid (biological assay) was passed down a column of IRA93 resin (chloride cycle; 100 ml). The column was washed with dilute acetic acid (0.25 M; 200 ml), water (750 ml) and eluted with aqueous lithium chloride solution (1 M). The first 150 ml of eluate, containing 0.28 g clavulanic acid (biological assay) was concentrated under reduced pressure to 15 ml and stored at 4° C. overnight. The product was filtered, washed successively with ethanol, acetone and diethyl ether before drying in air to give 668 mg solid ($E_1^1$ 245) representing a yield from filtered broth of 47%.

EXAMPLE 16

Broth was fermented and filtered as in Preparation 3 and a sample of the filtered broth (2 l) containing 1.23 g clavulanic acid (biological assay) was passed down a column of IRA93 resin (chloride cycle; 240 ml). The column was washed with water (500 ml), propan-2-ol:water (5:1; 400 ml) and then eluted with 5% (w/v) lithium chloride in propan-2-cl:water (5:1). The first 970 ml of eluate was concentrated under reduced pressure to 100 ml and stored at 4° C. for 2 days. The product was filtered and washed as in Example 15 to give 286 mg solid ($E_1^1$ 662) representing a yield from filtered broth of 19%.

EXAMPLE 17

Broth was fermented and filtered as in Preparation 3, 500 ml of the filtrate was loaded onto an IRA93 (chloride cycle; 50 ml). The column was washed with water (50 ml) and 95% aqueous ethanol (100 ml), before eluting with lithium chloride (1% w/v in 95% aqueous ethanol; 50 ml fractions). Fractions 2 and 3 were bulked and evaporated under reduced pressure until a solid material started to crystallise. The concentrate was chilled at +4° C. for $\frac{3}{4}$ h, and the solid was collected on a sinter filter. The solid was washed with ethanol, acetone and diethyl ether and dried for $\frac{1}{2}$ h at room temperature in a vacuum oven to give 89 mg lithium clavulanate ($E_1^1$ 770), representing a yield of 32% on the filtered broth.

EXAMPLE 18

Charcoal eluate prepared as in Preparation 3 (5 liters) was passed down a column of IRA68 (500 ml bed volume) in the chloride cycle at 1 liter/h. The column was washed with water (1 liter) and eluted with 0.5 M sodium chloride solution. The first liter of eluate was concentrated by rotary evaporation to 90 ml. A portion of the concentrate (10 ml) was treated with propan-2-ol (50 ml) with stirring. The supernatant was decanted from the tarry precipitate thus formed, concentrated by rotary evaporation to a volume of 3 ml and treated with 3 ml 30% w/v lithium chloride solution. After standing at 4° C. overnight product was filtered, washed successively with ethanol, acetone and diethyl ether and dried to give a white powder, 280 mg, with $E_1^1$ 770.

EXAMPLE 19

Lithium clavulanate ($E_1^1$ 667; 2.0 g prepared as in Example 15 with subsequent treatment with isopropyl alcohol) was dissolved in water (16 ml) and filtered; ethanol (64 ml) was added carefully and the mixture stirred at ambient temperature for 1 h. The precipitate initially formed contained no lithium clavulanate as determined by u.v. spectroscopy and was discarded. The supernatant was diluted with saturated lithium chloride solution (16 ml) and set aside to crystallize for 2½ h. The crystals were harvested by filtration, sucked dry, washed with acetone (2×15 ml), diethyl ether (2×20 ml) and dried in vacuo to constant weight (1.350 g) ($E_1^1$=735).

Pharmaceutical Example 1

Lithium clavulanate (100 mg) is dissolved in physiological saline (10 ml) and thoroughly mixed with a solution of cephaloridine (100 mg) in physiological saline (10 ml) to give a solution suitable for injection.

Pharmaceutical Example 2

A composition similar to that of Pharmaceutical Example 1 was prepared but the lithium clavulanate was replaced by sodium clavulanate (100 mg).

Pharmaceutical Example 3

Lithium clavulanate (100 mg) is dissolved in physiological saline (10 ml) and thoroughly mixed with a solution of ampicillin (100 mg) in physiological saline (10 ml) to give a solution suitable for injection.

We claim:

1. Potassium clavulanate of the formula

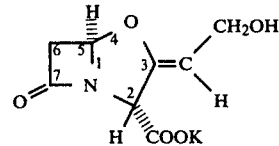

having a molar extinction coefficient as determined in 0.1 M aqueous potassium hydroxide using ultraviolet light of wavelength 258 nm of about 17000.

* * * * *